United States Patent [19]
Marshall et al.

[11] Patent Number: 5,996,396
[45] Date of Patent: Dec. 7, 1999

[54] APPARATUS FOR DETERMINING ODOR LEVELS IN GAS STREAMS

[75] Inventors: Stephen Edward Marshall, Conroe; Glenn Scott Selman, Spring; Christopher Lee Skubis, The Woodlands, all of Tex.

[73] Assignee: Y-Z Industries Sales, Inc., Snyder, Tex.

[21] Appl. No.: 09/121,512

[22] Filed: Jul. 23, 1998

[51] Int. Cl.$^6$ ........................................... G01N 7/00
[52] U.S. Cl. ............................................... 73/23.34
[58] Field of Search .................................. 73/23.34, 202; 423/405; 436/7; 252/408.1; 422/83

[56] References Cited

PUBLICATIONS

Heath Consultants Incorporated, Instruction Manual for HeathTech Odorator Natural Gas Odor Analyzer; Part No. 0715630; May 1995.
Bacharach, Inc.—Odorometer Instruction Manual Portable Gas Odorant Tester; Instruction 23–9125; Jan. 1990.
Heath Consultants Incorporated, Instruction Manual for Natural Gas Odorator; Aug. 1987.
American Gas Association, Engineering Technical Note, Natural Gas Odorization: Compliance with Federal Regulations; CAS–2–1–95.

*Primary Examiner*—Jay L. Politzer
*Attorney, Agent, or Firm*—David H. Judson

[57] ABSTRACT

A microprocessor-based apparatus is provided for determining odor levels in gas streams. The apparatus includes a mixing chamber for mixing gas from a gas supply to be tested with air to form a gas-air mixture. The mixing chamber includes a gas inlet port through which the gas is received, an air intake port through which the air is received, and an outlet port through which the gas-air mixture leaves the mixing chamber. The apparatus includes a flow control valve that can be connected to the gas supply to enable a user to selectively adjust the flow rate of the gas from the gas supply to the apparatus. The apparatus also includes a mass flow sensor positioned between the flow control valve and the gas inlet port of the mixing chamber for measuring the mass flow rate of the gas flowing into the mixing chamber. A motorized fan is positioned in a conduit connected to outlet port of the mixing chamber for drawing the gas-air mixture out of the mixing chamber to a location where it can be sniffed by the user to detect odor. The apparatus also includes a tachometer for measuring the rotational speed of the motorized fan and a microprocessor controller responsive to signals from the tachometer for controlling the rotational speed of the motorized fan such that it is maintained at a substantially constant speed. The apparatus can be linked to a personal computer to enable data to be exchanged between the personal computer and the apparatus.

18 Claims, 16 Drawing Sheets

| Date | Time | Location | TOT | DOT | Operator | Comments |
|---|---|---|---|---|---|---|
| 02/01/98 | 09:00:00 | ACME TREE SER... | 0.23 | 0.37 | JOSEPH... | |
| 02/02/98 | 09:00:00 | ALBERTSONS S... | 0.41 | 0.51 | JOSEPH... | |
| 02/03/98 | 09:00:00 | EMERSON ELEM... | 0.18 | 0.34 | HENRY... | |
| 02/05/98 | 09:00:00 | EMERSON ELEM... | 0.33 | 0.42 | JOHN M... | |
| 02/08/98 | 09:00:00 | ACME TREE SER... | 0.31 | 0.42 | JOHN M... | |
| 02/09/98 | 09:00:00 | ALBERTSONS S... | 0.46 | 0.57 | JOHN M... | |
| 02/10/98 | 09:00:00 | EMERSON ELEM... | 0.11 | 0.31 | HENRY... | |
| 02/12/98 | 09:00:00 | EMERSON ELEM... | 0.23 | 0.34 | JOHN M... | |
| 02/15/98 | 09:00:00 | ACME TREE SER... | 0.18 | 0.30 | JOSEPH... | |
| 02/15/98 | 09:00:00 | QUALIFICATION... | 0.31 | 0.44 | JOSEPH... | |
| 02/15/98 | 09:00:00 | QUALIFICATION... | 0.30 | 0.48 | HENRY... | |
| 02/15/98 | 09:00:00 | QUALIFICATION... | 0.40 | 0.48 | JOHN M... | |
| 02/16/98 | 09:00:00 | ALBERTSONS S... | 0.34 | 0.46 | JOSEPH... | |
| 02/17/98 | 09:00:00 | EMERSON ELEM... | 0.14 | 0.30 | HENRY... | |
| 02/19/98 | 09:00:00 | EMERSON ELEM... | 0.25 | 0.34 | JOHN M... | |

APPARATUS FOR DETERMINING ODOR LEVELS IN GAS STREAMS

BACKGROUND OF THE INVENTION

1. Technical Field

The present invention relates generally to apparatus for determining odor levels in odorized gas streams.

2. Description of the Related Art

Federal and state regulations require that combustible gases (e.g., natural gas) in transmission lines be odorized to provide a quick and easy means for detecting the presence of gases. Odorization involves adding small amounts of a chemical with a distinctive odor to the gas stream. This odor facilitates leak detection and provides an early warning of potentially unsafe conditions.

The odor must be readily detectable by a person with a normal sense of smell when gas is present at a given concentration in air. The concentration is typically specified as a certain percentage of the lower explosive limit (LEL) of the gas.

Federal and state odorizing regulations require gas operators to conduct periodic sampling at distribution sites to assure proper odor levels. Portable instruments, sometimes referred to as odorometers, have been devised to determine gas odor levels using olfactory testing. These instruments are available from a number of manufacturers including Bacharach, Inc. and Heath Consultants, Inc.

In one known device, gas to be analyzed enters the instrument through a gas intake port. The gas passes through a low pressure regulator and then a flow adjustment valve, which is operated by a user. The gas then enters a sensor chamber, which measures gas flow. A signal from the sensor chamber is processed, converted to a digital signal and fed to a liquid crystal display (LCD). The gas from the sensor chamber is then mixed with air drawn in by an air blower. The air-gas mixture then exits the device through an exhaust port, where it can be sniffed by a user.

One test that is commonly performed with such a device is known as a threshold odorant test (TOT). This test is used to determine a threshold gas-air concentration at which odor is barely detectable. In this use, the operator slowly opens the flow adjustment valve, allowing the gas sample to enter the instrument, while at the same time breathing normally with his or her nose placed close to the exhaust port. When odor in the sample is detected, the operator depresses a read button to observe a reading on the LCD corresponding to gas flow. A look-up chart is then used to convert the reading into a percent gas concentration, which is then hand-written somewhere for recordation.

Another use of the device is to determine odor characteristics at given gas-air concentrations. In this use, a gas/air mixture at a preset concentration is sniffed by various persons who then categorize the odor level as "absent," "barely detectable," "readily detectable," "strong" or "obnoxious."

A significant problem with these known devices it that they fail to provide accurate and repeatable gas concentration readings. Except for the LCD output, the instruments are substantially analog devices and lack adequate control means to ensure steady operation. For instance, the fans or blowers used to draw air through the devices cannot be sufficiently controlled to ensure constant speed, which is critical in determining gas concentration.

Furthermore, the known devices fail to provide adequate mixing of the sample gas and air. Consequently, the gas-air mixtures are not uniformly mixed, resulting in testing inaccuracies.

In addition, known devices are not equipped with recording means for storing and/or analyzing test data. Consequently, users must hand-write the data somewhere and use a look-up table to cross-reference data with gas concentration values. This is a potential source for further errors.

BRIEF SUMMARY OF THE INVENTION

Thus, a primary object of the invention is to provide a device for determining odor levels in gas streams that produces highly accurate and repeatable results.

Another object of the invention is to provide a device for determining odor levels that is microprocessor based.

A further object of the invention is to provide a device for determining odor levels that thoroughly mixes the gas sample to be tested with air.

Yet another object of the invention is to provide a device that automatically records test data and is thereby substantially "paper-free."

A further object of the invention is to provide a device that analyzes test data, obviating the need for look-up tables and data interpretation.

A further object of the invention is to provide a device that can download test data stored therein to a personal computer (PC) for analysis, report preparation and storage in a main database.

Still another object of the invention is to provide a device that can be linked to a printer to print data stored in the device.

Yet another object of the invention is to provide a device that can be uploaded with data such as test location and technician information from a PC.

These and other objects are accomplished by utilizing a microprocessor-based odorometer for correlating odor levels in gas streams with gas in air concentrations in accordance with the invention. The device includes a mixing chamber for mixing gas from a gas supply to be tested with air to form a gas-air mixture. The mixing chamber includes a gas inlet port through which the gas is received, an air intake port through which the air is received, and an outlet port through which the gas-air mixture exits the mixing chamber. A static mixing element is located at the air intake port to cause turbulence in incoming air flow to promote thorough mixing of the air and gas. The device includes a flow control valve that is connected to the gas supply to enable a user to selectively adjust the flow rate of the gas entering the device. A mass flow sensor is positioned between the flow control valve and the gas inlet port of the mixing chamber for accurately measuring the mass flow rate of the gas flowing into the mixing chamber. A motorized fan is positioned in a hose connected to outlet port of the mixing chamber for drawing the gas-air mixture out of the mixing chamber and moving it to a sniff chamber, where it can be sniffed by the user to detect odor.

The device is equipped with a microprocessor controller including a tachometer for determining the rotational speed of the motorized fan. The microprocessor controller is responsive to signals from a fan speed sensor for controlling the rotational speed of the motorized fan such that it is maintained at a substantially constant speed. Consequently, there is substantially constant air flow into the device.

A rechargeable lead-acid battery is provided for powering the instrument.

The device includes memory for storing test data. It is equipped with a keypad and an LCD display for user interface.

The device displays test results in actual air/gas percentages, eliminating the need for look-up charts.

The device records complete test results electronically. It can also record any comments by technicians relating to a given test such as, e.g., information on weather conditions at a test site. In addition, test records are stamped with date/time information as well as information on device calibration.

The apparatus can be linked to a PC to enable test and device data to be exchanged between the PC and the apparatus. A software package is provided for the PC to generate reports, graphs, and data archives from data read from the device. The device thus eliminates the need to manually write test reports. In addition, critical test data recorded by the device cannot be altered using the device. This feature substantially reduces the risk of test data being falsified by technicians.

Test data downloaded from the device to a PC can also be exported to third-party developed applications for further processing.

In addition, the software package allows user, test location and calibration information to be easily uploaded from the PC to the device. This feature eliminates the need for technicians to prepare forms and perform repetitive data entry.

The device also includes a user authentication feature. Each user is required to enter an identification and corresponding password before the device can be used.

BRIEF DESCRIPTION OF THE DRAWINGS

For a more complete understanding of the present invention and the advantages thereof, reference should be made to the following Detailed Description taken in connection with the accompanying drawings, in which:

FIG. 10 is an exemplary screen shot generated by the PC software of a test log;

FIG. 14 is an exemplary screen shot generated by the PC software showing details of a given test conducted using the device;

FIG. 16 is an exemplary screen shot generated by the PC software showing details of a qualification test taken by a given user.

DETAILED DESCRIPTION OF THE PREFERRED EMBODIMENT

Figure 1:
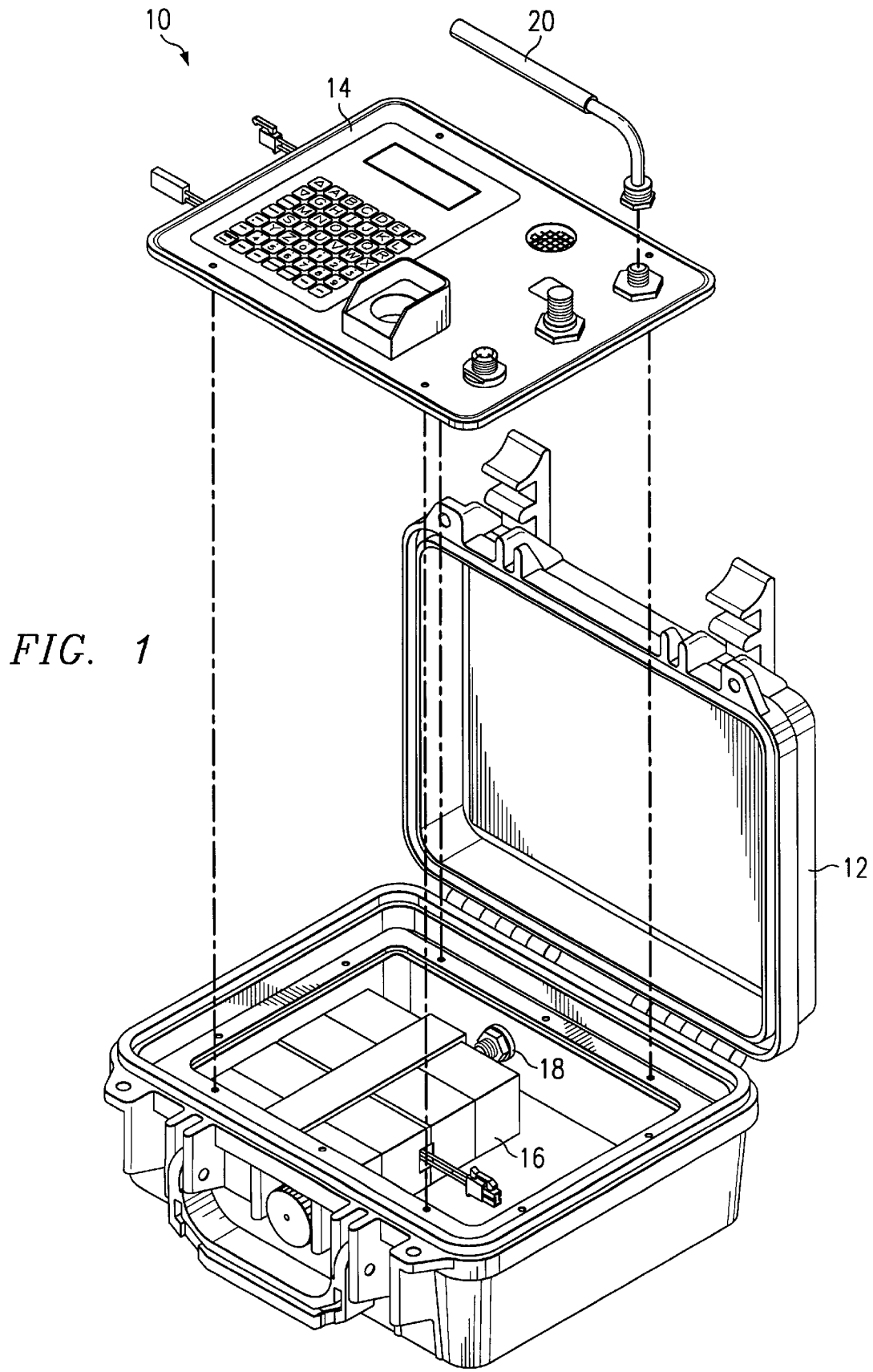
FIG. 1 is an exploded perspective view of a device for determining odor levels in accordance with the invention.

FIG. 1 is an exploded view of an odorometer device or instrument 10 for correlating odor levels in gas streams with gas in air concentrations in accordance with the invention. The device 10 includes a portable outer housing or case 12. The case 12 is equipped with a main unit 14 and a battery 16 for powering the unit. The battery 16 is preferably a rechargeable lead-acid battery. A charger port 18 is provided in the case 12 so that the battery 16 can be charged in situ. Use of a battery facilitates portability of the device, though it should be noted that the device can be configured to be AC powered if desired.

An inlet hose 20 is optionally included to facilitate coupling of the instrument with a gas supply or source (not shown in FIG. 1) to be tested. A variety of odorized gases can be tested including, e.g., natural gas and liquefied petroleum gas such as propane and butane.

Figure 2:
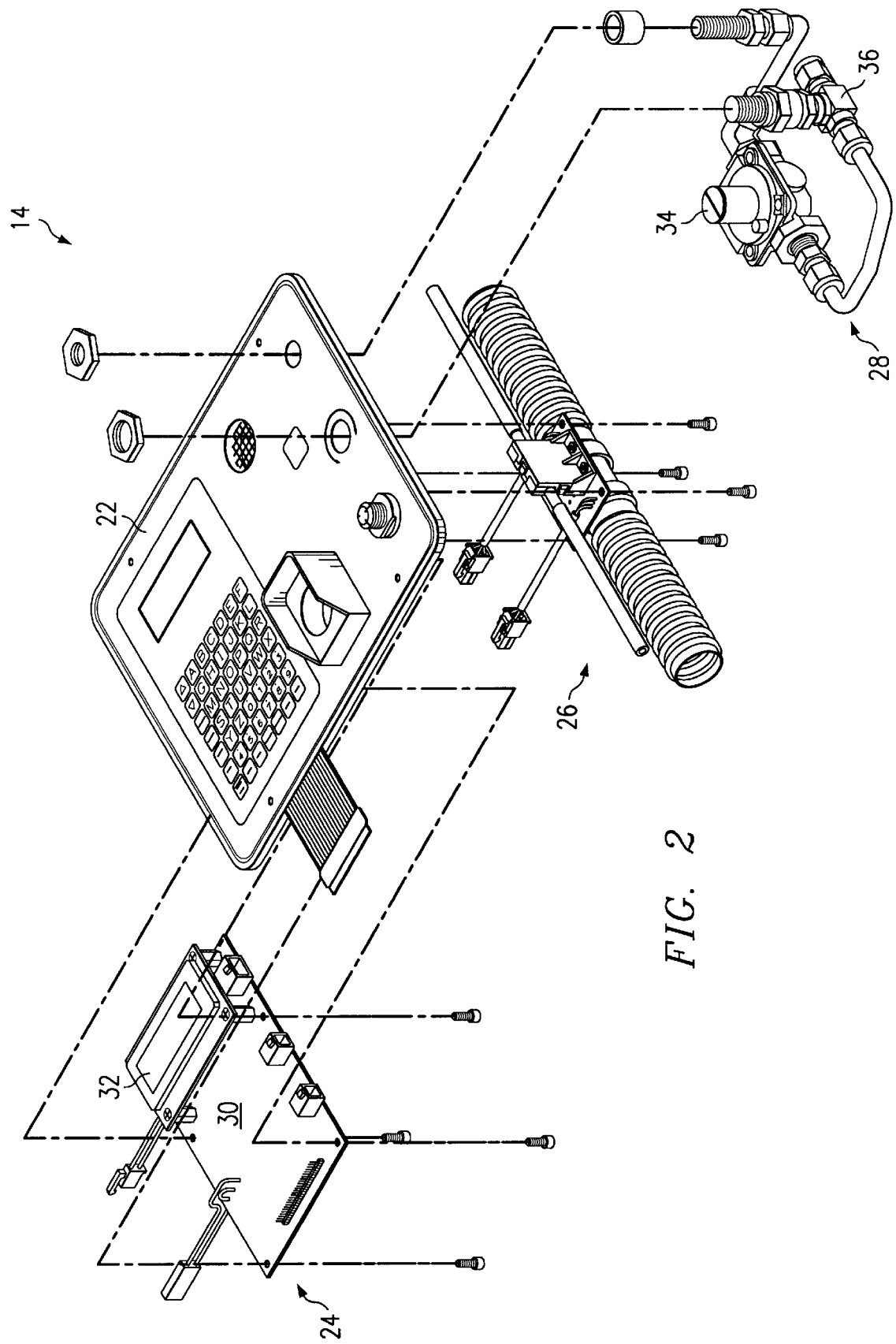
FIG. 2 is an exploded perspective view of the main unit assembly shown in the FIG. 1.

FIG. 2 is an exploded view showing the main unit assembly 14 in greater detail. The main unit assembly 14 includes a mounting panel assembly 22, a main printed circuit board (PCB) assembly 24, a fan sub-assembly 26, and a regulator assembly 28.

The main PCB assembly 24 includes a processor board 30 containing the microprocessor circuitry for controlling and operating the instrument as will be described further below. The main PCB assembly 24 also includes a 4×20 character LCD display 32.

The regulator assembly 28 comprises a low flow regulator 34 for regulating the pressure of gas from the gas supply. It also includes a flow control valve 36, preferably a precision needle valve, that can be adjusted by a user to control the flow rate of gas from the gas supply.

Figure 3:
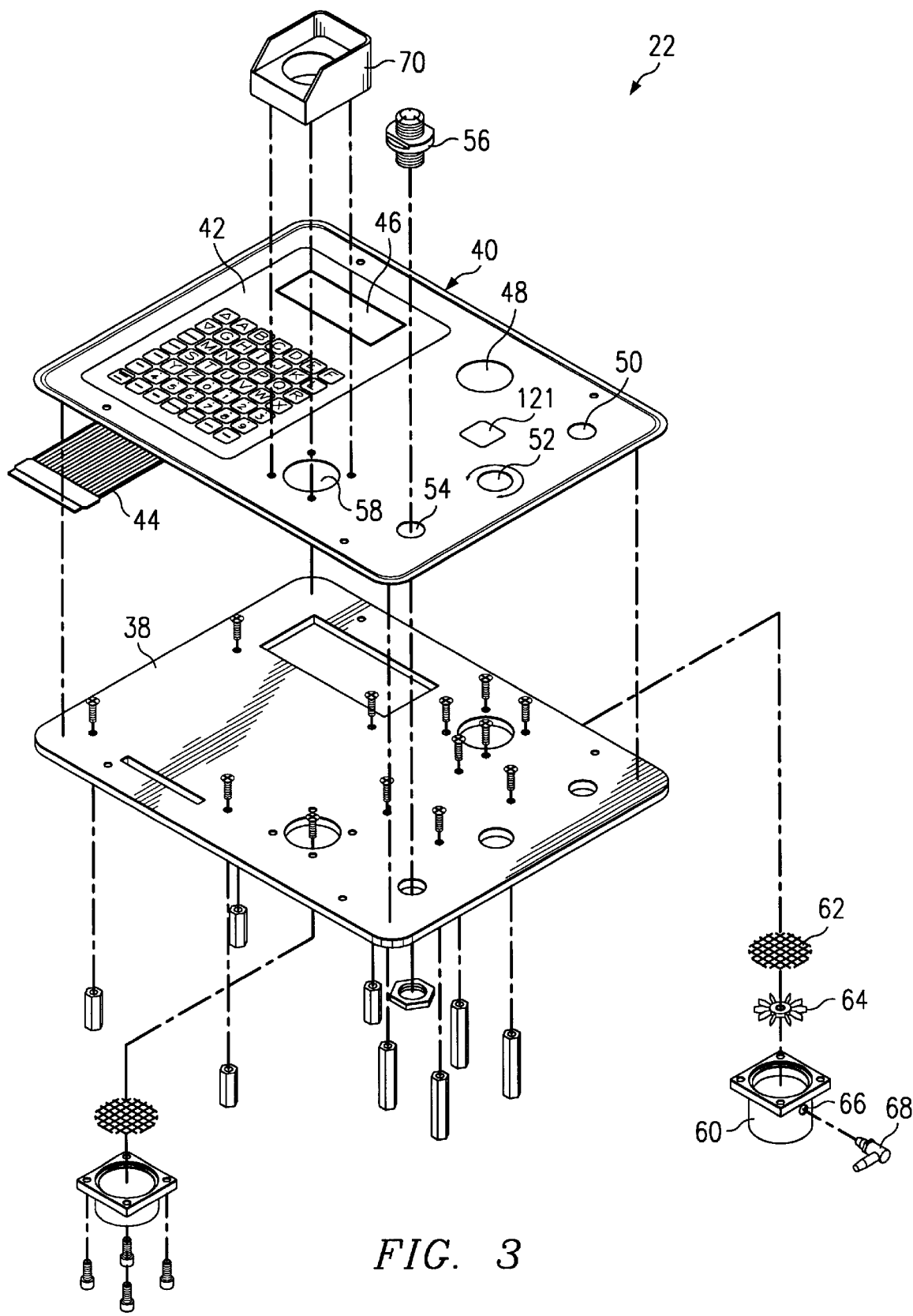
FIG. 3 is an exploded perspective view of the mounting panel assembly of the main unit assembly.

FIG. 3 illustrates the mounting panel assembly 22 in greater detail. The mounting panel assembly 22 comprises a base panel 38 and an overlay panel 40. The overlay panel 40 includes a membrane keyboard or keypad 42 having a 7×7 matrix. A connector cable 44 from the keypad 42 connects to the main PCB assembly 24. The base and overlay panels 38, 40 include a window 46 through which the LCD display 32 can be viewed. It also includes an air intake port 48, a gas inlet port 50, an opening 52 for receiving an adjustment knob of the flow control valve 36, an opening 54 for receiving a data port connector 56, and a gas outlet port 58.

The air intake port 48 leads to a mixing chamber 60 directly therebeneath. A screen 62 and a mixing element 64, preferably comprising a static (i.e., non-rotating) fan, are positioned at the air intake port 48. It should be noted that other types of mixing elements can alternatively be used, e.g., a series of baffles. The mixing chamber 60 includes a gas entry port 66 through which gas enters the mixing chamber at a location slightly below the fan element 64. A polyethylene elbow tube 68 supplies gas to the gas entry port 66.

A nose piece 70, which forms a "sniffing chamber" at which gas is sniffed by a user, is connected to the outlet port 58.

Figure 4:
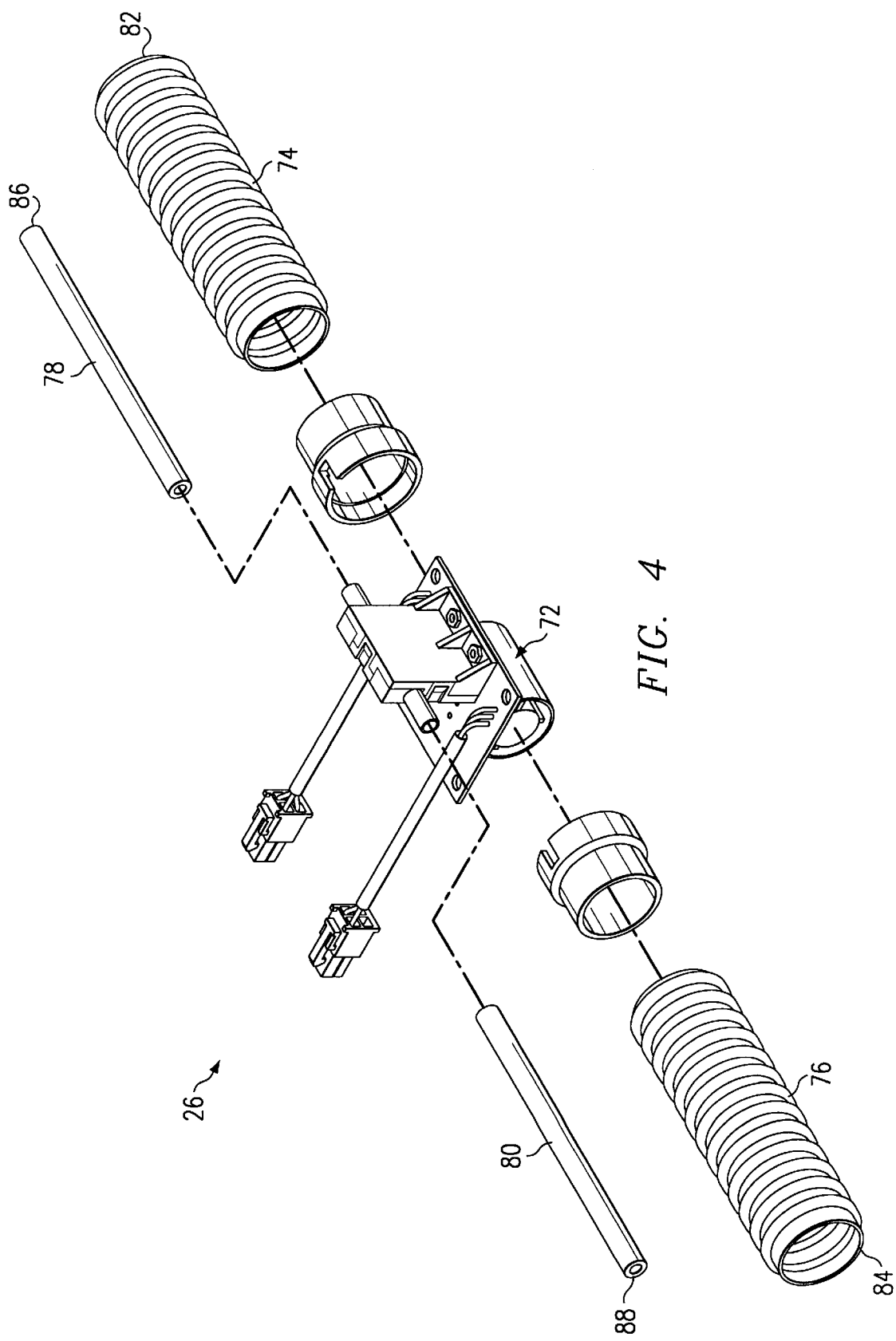
FIG. 4 is an exploded perspective view of the fan sub-assembly of the main unit assembly.

FIG. 4 is a detailed exploded view of the fan sub-assembly 26 (of FIG. 2). The fan sub-assembly 26 comprises a fan PCB assembly 72, which is connected on opposite sides by first and second conduits or hoses 74, 76 and first and second tubes 78, 80.

The hoses 74, 76 are preferably flexible polypropylene hoses, each having a length of four inches and a one-inch inner diameter. The inlet end 82 of the first hose 74 connects directly with the mixing chamber 60 to receive flow therefrom. The outlet end 84 of the second hose 76 connects directly with the gas outlet port 58 for exhausting gas from the device 10.

The tubes 78, 80 are preferably of quarter-inch outer diameter, each having an eight-inch length. The inlet end 86 of the first tube 78 is connected to the outlet of the flow control valve 36. The outlet end 88 of the second tube 80 is connected to the elbow tube 68 leading to the mixing chamber 60.

Figure 5:
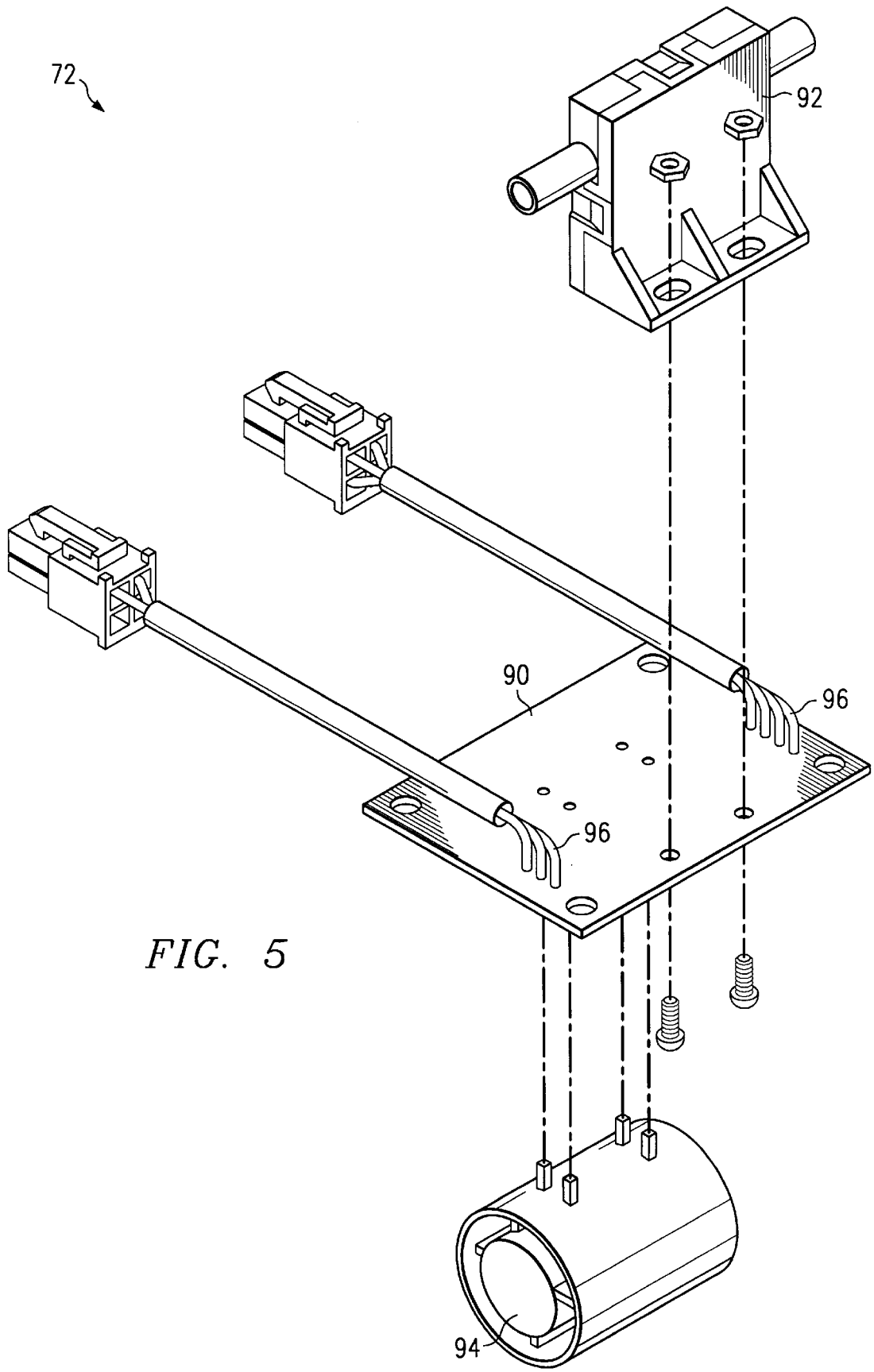
FIG. 5 is an exploded perspective view of the fan printed circuit board assembly of the fan sub-assembly.

The fan PCB assembly 72 (of FIG. 4) is shown in greater detail in FIG. 5. The fan PCB assembly 72 includes a printed circuit board 90, on which a mass flow sensor 92 and a motorized fan 94 are connected. The mass flow sensor 92 is connected on opposite sides to the tubes 78, 80 to measure flow of gas therethrough. The mass flow sensor 92 transmits signals indicative of the gas flow rate through circuitry on the PCB 90 to the microprocessor controller on the main PCB assembly 24.

Also mounted on the PCB 90 is a fan speed sensor 96, preferably an infrared device. The sensor 96 includes an infrared emitter/receiver pair located on opposite sides of the fan 94. The emitter sends an infrared beam to the receiver. The beam is interrupted each time a fan blade crosses it as the fan 94 rotates. A pulsed signal indicative of the fan rotation speed is thereby transmitted by the sensor 96 to a tachometer 97 in the microprocessor controller. A closed loop control circuit comprising the infrared sensor/tachometer and a digitally controlled drive circuit are used to keep the fan at a constant speed. The main controller can adjust the fan speed as necessary by outputting a signal to a digital potentiometer in the main PCB 24 to adjust the drive voltage to the fan 94.

Figure 6:
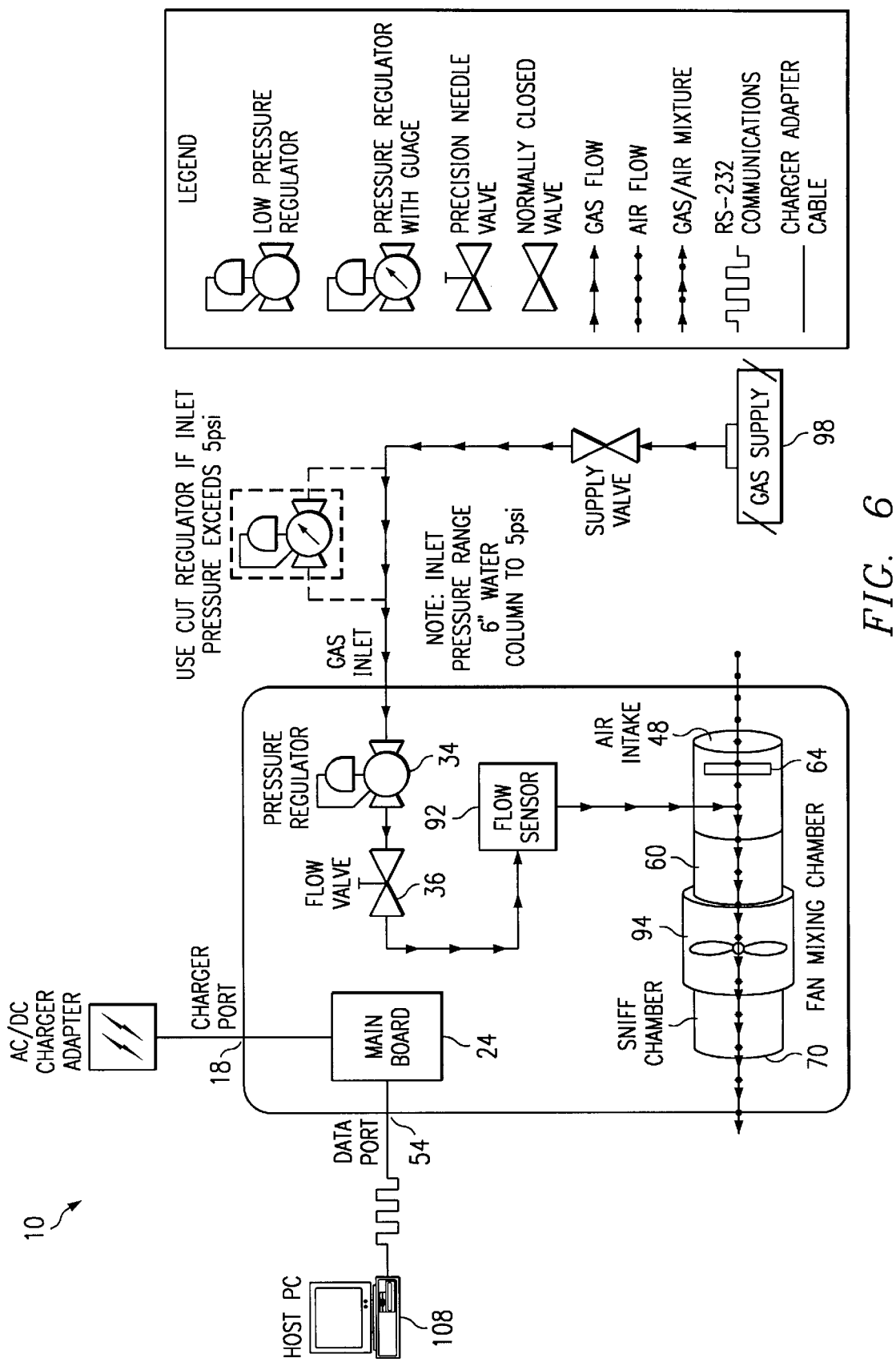
FIG. 6 is a schematic diagram illustrating gas and air flow through the device.

Referring now to FIG. 6, the path of air and gas flow through the device 10 will now be described. Gas from a gas supply 98 flows through tubing leading to the regulator 34. The gas flows through the regulator 34 and thereafter through the flow control valve 36 (when it is open). Thereafter, gas flows through the inlet end 86 of first tube 78 and then through the mass flow sensor 92, which determines its flow rate. Thereafter the gas flows through the second tube 80 which is connected to the elbow tube 68 leading to the mixing chamber 60, where the gas is mixed with air.

Air enters the instrument 10 through the air inlet port 48 shown in FIG. 3. It flows through the screen 12 and past the stationary fan element 64 into the mixing chamber 60. The fan element 64 is designed to swirl incoming air thereby creating turbulence to promote mixing with incoming gas. The air and gas are mixed in the mixing chamber 60 to form a mixed gas/air mixture, which flows into the inlet end 82 of the first hose 74. The air/gas mixture is drawn through the hose 74 by the motorized fan 94 and forced through the second hose 76, which is connected to the outlet port 58. The gas/air mixture flows through the outlet port and out of the nose piece 70 forming the sniff chamber.

Figure 7:
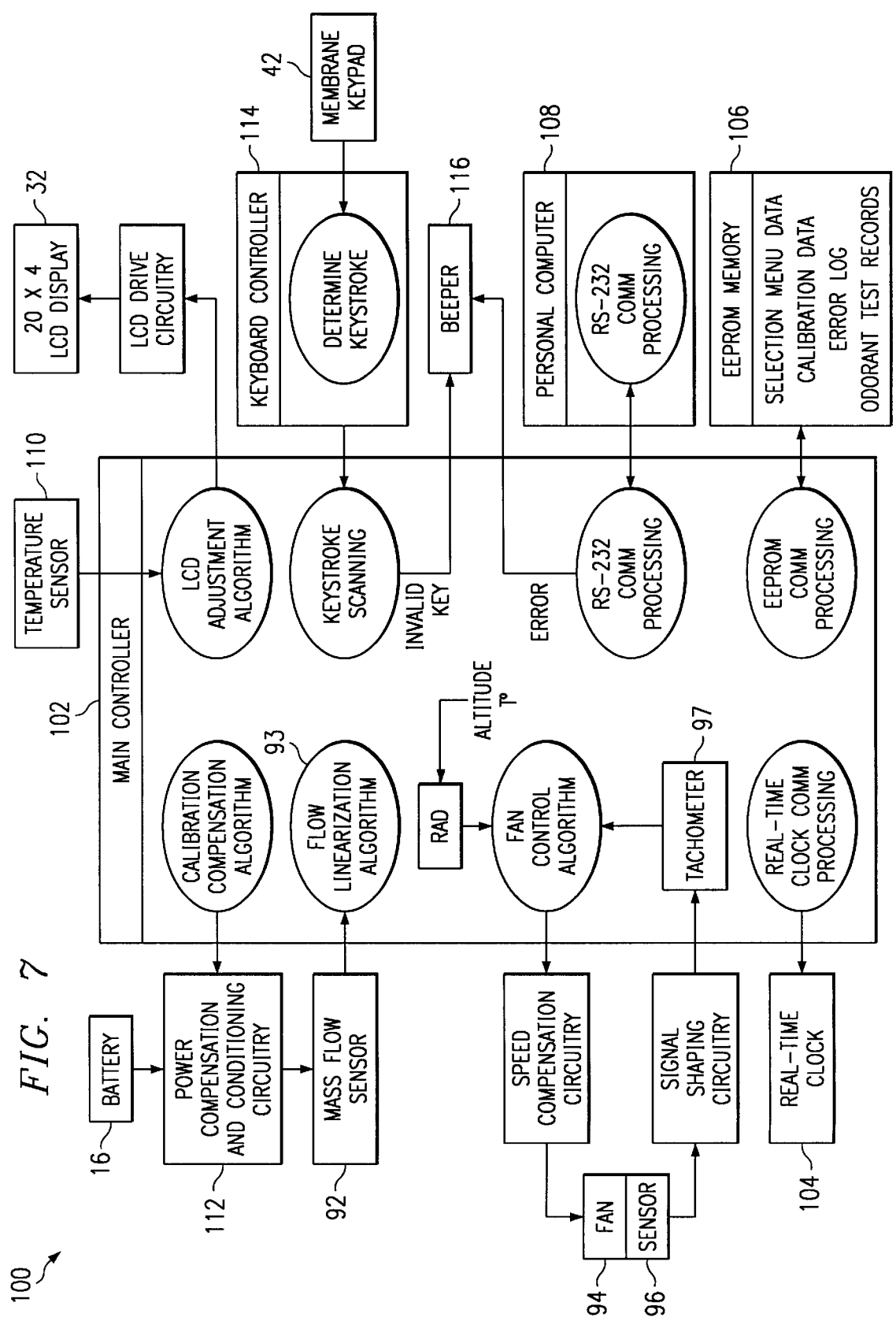
FIG. 7 is a schematic block diagram illustrating microprocessor control of the device.

FIG. 7 is a block diagram illustrating the microprocessor circuitry 100 for controlling various components of the device 10. The circuitry 100 includes a main controller 102, which along with associated firmware, monitors all the system data inputs and provides control and data outputs for various system devices. An on-chip analog to digital (A/D) converter is used to convert critical analog inputs to digital signals for processing. A timer input captures the tachometer pulses from the motorized fan assembly. Digital potentiometers are used to provide voltage controlled outputs for contrast adjust (for the LCD), fan speed and flow sensor offset and span.

The device 10 also includes a real time clock chip 104 to keep current date and time information. The real time clock 104 enables test results and errors to be date and time stamped for record keeping purposes. A battery backup keeps the date and time on the clock chip 104 current when power is off.

The device 10 further includes a non-volatile memory, preferably at least one electrically erasable, programmable read-only memory chip (EEPROM) 106 to store user information, test location, test records, error logs, and calibration/parameter data. The EEPROM 106 can be uploaded to or downloaded from by a PC 108 using a software package, which will be further described below. This allows for a paperless audit trail. For convenience, user and test location information can be written to the EEPROM 106 by the PC 108 to reduce user data entry in the field.

Ambient temperature readings from an onboard temperature sensor 110 are monitored by the microprocessor controller 102 and used to automatically adjust the LCD display contrast with temperature variations. Adjustments are made using a digital potentiometer.

The device 10 also includes battery compensation and conditioning circuitry 112, which automatically compensates for battery voltage level changes. The circuitry 112 can include, e.g., a voltage regulator. Battery compensation allows a wider range of battery voltage to be used while maintaining the calibration accuracy of the flow sensor 92 and increasing the charge life of the battery 16.

The device 10 uses a flow linearization algorithm 93 using a multi-point calibration process of the mass flow sensor readings to provide a linear flow response. The LCD 32 can thus display gas-in-air concentrations, obviating the need for a user to cross-reference readings with a look-up table.

A keyboard controller 114 is used as a keyboard decoder. The keyboard controller 114 scans the keyboard 42 for a key press and then communicates the key press to the main controller 102. If an invalid key is pressed, a beeper 116 is activated to notify the user of the error.

The device 10 can be linked to the PC 108 through the data port 54. The PC 108 includes a software package used as an interface tool to allow uploading and downloading of data to/from the device 10. Stored test records, user information, test location information, and error logs can be read from the device and used to generate reports, graphs and data archives. Information on users, test locations, and device calibration can be uploaded from the PC 108 to the device 10.

The device 10 can also be configured to be linked through the data port 54 to a printer for printing data stored in the device.

Figure 8:
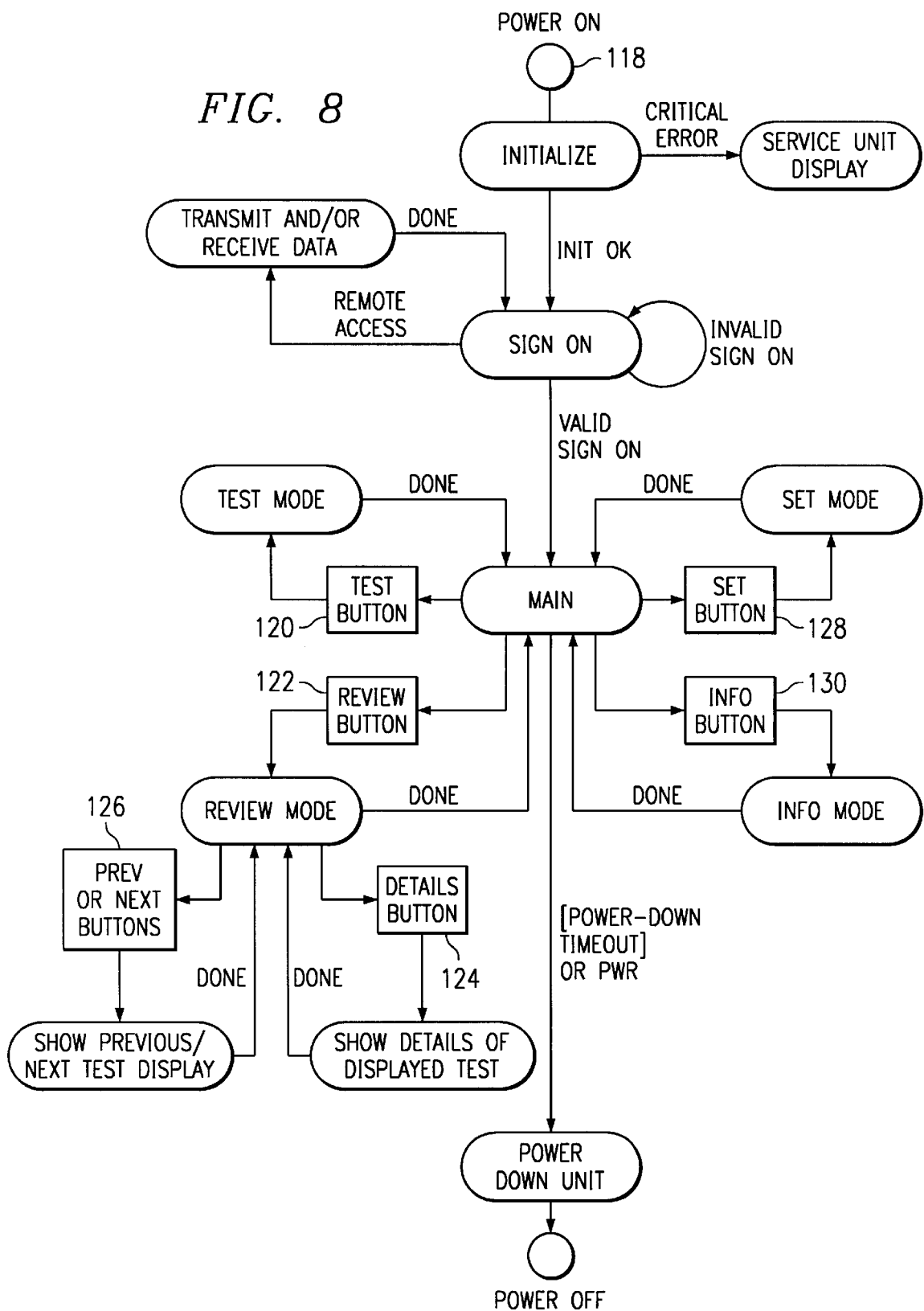
FIG. 8 is a high-level state diagram illustrating operation of the device.

FIG. 8 is a state diagram illustrating operation of the device 10 through keypad input. (The term "DTEX" used in the drawings is a trademark for the device 10.) Initially the user presses the "Power On" button 118 on the keypad 42 causing the system to initialize. If an error occurs during the initialization process, a "Service Unit" message is shown on the LCD 32. After the device 10 has been initialized, the user can (if desired) connect the device through the data port 54 to the PC 108 in order to transmit and/or receive data.

Thereafter, the user is prompted to "sign on," and after a valid sign on, the main mode is entered. The device includes a user authentication feature for security. For a valid sign on, each user is required to input identification information and a corresponding password.

If the user presses the "Test" button 120, the device 10 switches to the test mode and can be used to conduct testing. For example, threshold odor testing can now be conducted as follows. First, the user enters any needed information on the keypad, including, e.g., information identifying the gas supply location. Next, the inlet hose 20 is connected to the gas supply to be tested. Then, with the fan 94 having been turned on, the user gradually opens the gas flow valve 36, allowing the gas sample to enter the instrument 10. At the same time, the user breathes normally with his or her nose placed at the nose piece 70. When odor in the sample is detected, the user depresses a "Record Test Level" button 121 (shown in FIG. 3). The gas concentration reading is displayed on the display 32 and stored in device memory 106.

The user can enter any comments he or she may have relating to the test such as, e.g., wind conditions at the test site.

The user can press a "Review" button 122 to place the device 10 in a review mode, in which test results can be reviewed. If the "Details" button 124 is pressed, specific details of a particular test are displayed. The user can also press "Previous" or "Next" buttons 126 to scroll through other test information. While the user can review test data, the device 10 is programmed to prevent the user from altering critical test data in order to prevent any attempt to falsify data.

The "Set" button 128 can be pressed to set up new users and to set the system clock.

The "Info" button 130 can be pressed to switch to an information mode to, for example, look at the serial number of the unit, calibration data of the unit or the last reported error of the unit.

The device 10 can be powered down by the user or will automatically power down if no request has been made within a given period of time, for example, thirty minutes.

Figure 9:
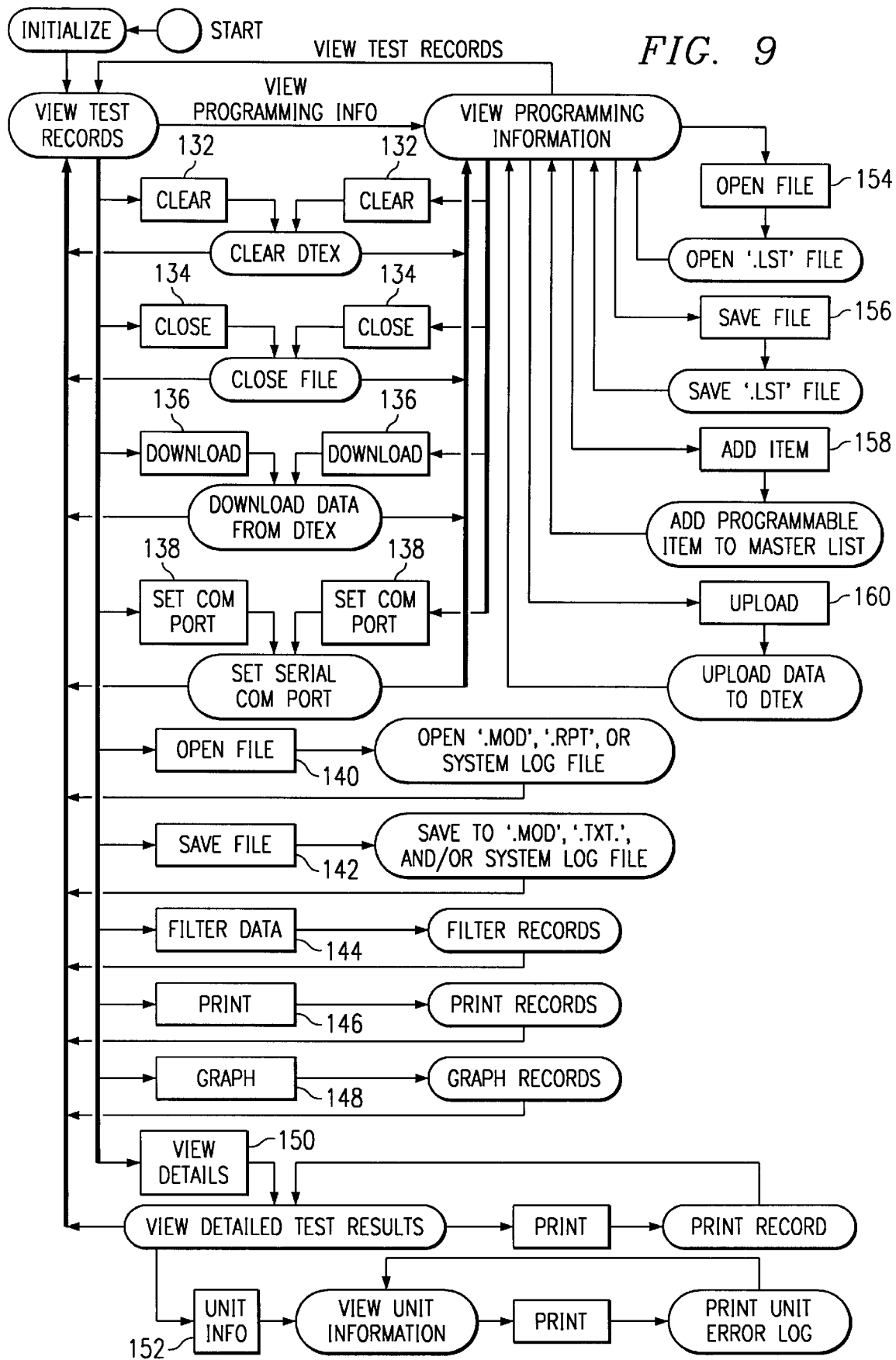
FIG. 9 is a high-level reporter state diagram illustrating operation of PC software for analyzing test data from and for programming the device.

After all the desired readings have been taken of gas samples, the instrument can be taken to a central location site and data stored therein can be downloaded to a PC 108. In accordance with the invention, Windows-based software is provided for the PC to prepare test data into formal reports needed to satisfy the formal reporting requirements. The data from the device can also be logged onto a main data base and retrieved as needed. The software also enables devices to be programmed. FIG. 9 is a high level state diagram illustrating use of the PC 108 for uploading and downloading data to/from a selected device once it has been linked to the PC 108 through the data port 54. After initialization, a user can view test records and programming information on the PC display. The software provides the user with several options for managing test records and device programming information. The user can use a pointing device such as a mouse to move a cursor on the PC display to select and click on various items. A "Clear" button 132 can be pressed to clear the memory (EEPROM) on the device 10. A "Close" button 134 can be pressed to close any opened file. A "Download" button 136 can be pressed to download data from the device memory. A "Set COM Port" button 138 can be pressed to change the serial COM port as desired.

An "Open File" 140 button can be pressed to open one of three different types of files. The ".MOD" files mirror the files stored in the device. The ".RPT" file contains an archive of test results. The "System Log" file is a master database of all tests run at all sites. FIG. 10 is an exemplary screen shot generated by the PC software of a test log.

Figure 11:
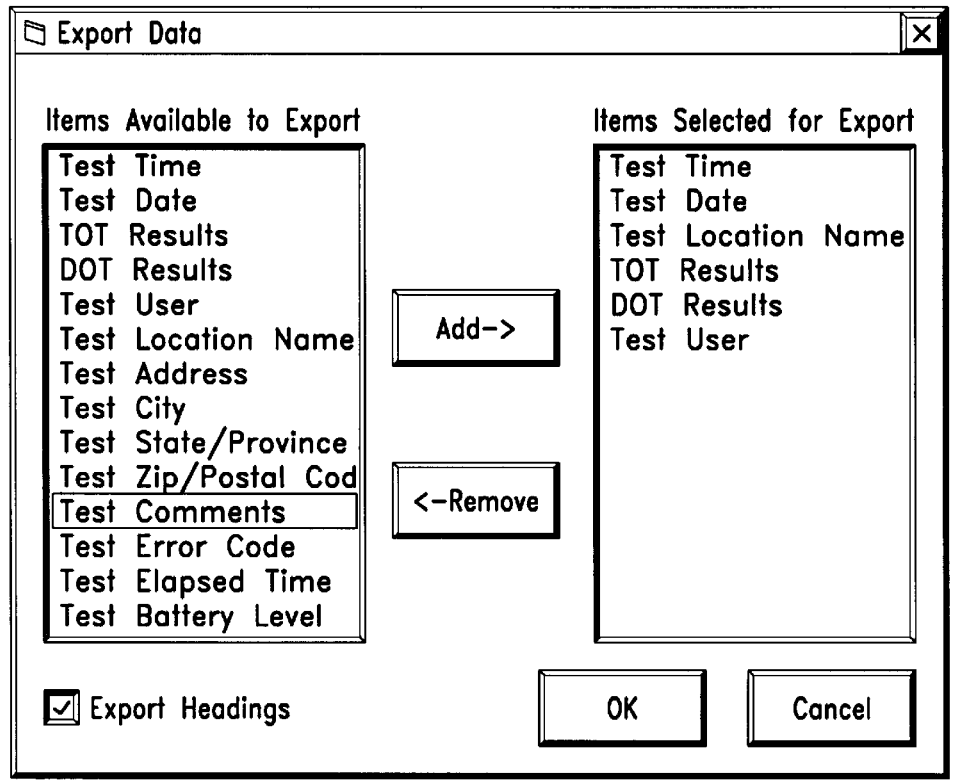
FIG. 11 is an exemplary screen shot generated by the PC software illustrating exporting of data to external applications.

The "Save File" button 142 can be pressed to save test records in different file types, including ".TXT" files, which can be e-mailed if desired. The files can also be imported into third party developed software. FIG. 11 is an exemplary screen shot illustrating exporting of data to such third party applications.

Figure 12:
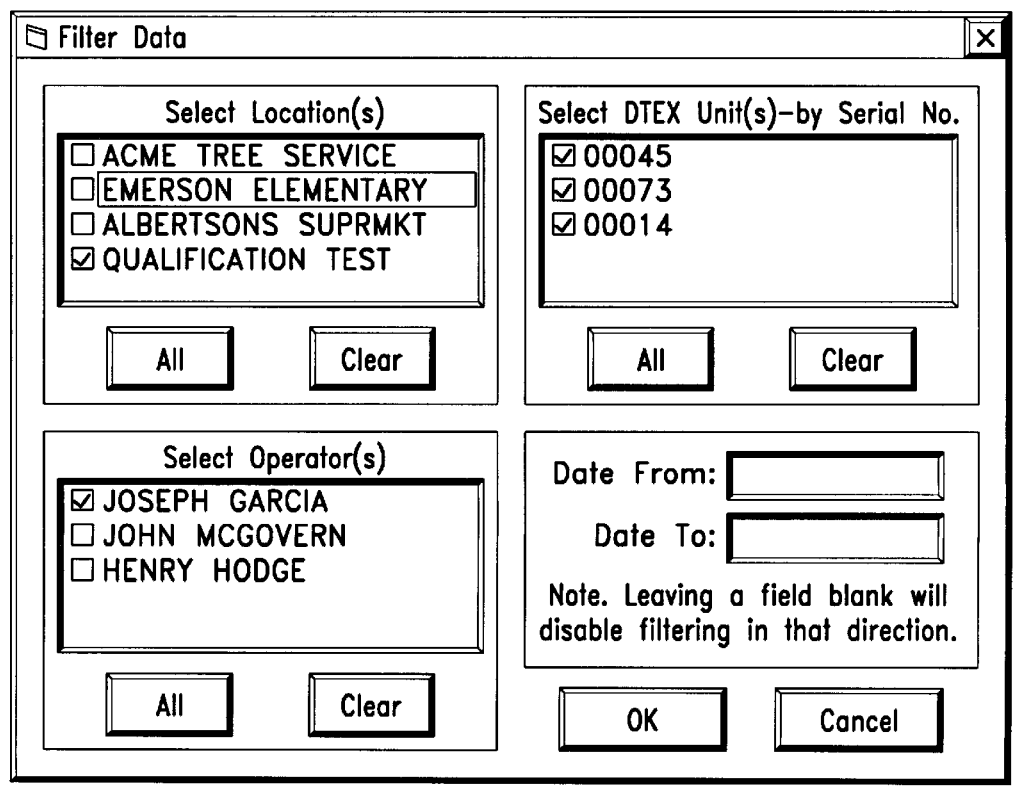
FIG. 12 is an exemplary screen shot generated by the PC software illustrating data filtering.

A "Filter Data" button 144 can be pressed to allow stored records to be filtered (i.e., queried) by, e.g., test date, user name, test location and particular unit used. FIG. 12 is an exemplary screen shot illustrating data filtering.

A "Print" button 146 can be pressed to print a file.

Figure 13:
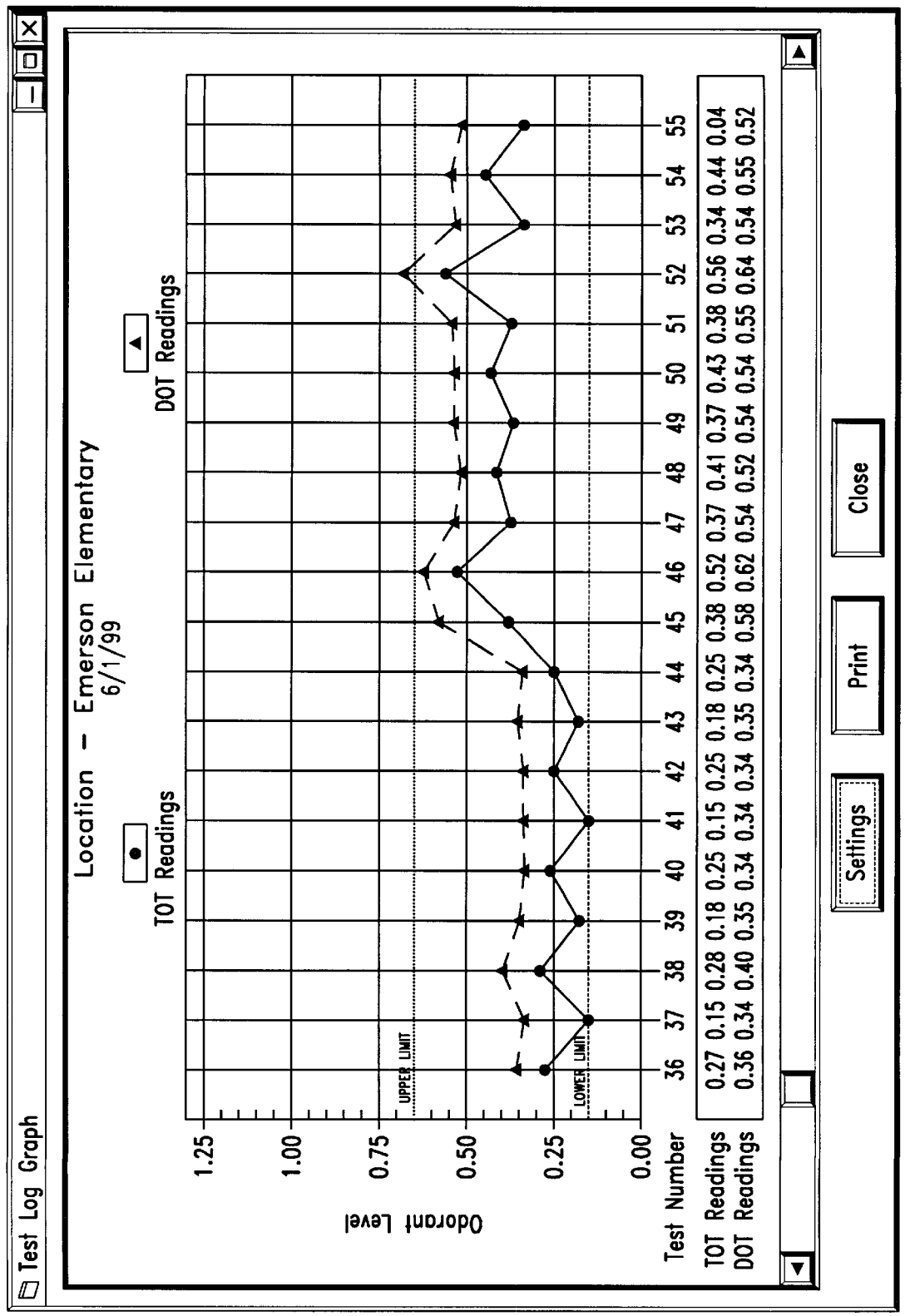
FIG. 13 is an exemplary screen shot generated by the PC software of a graph of test readings at a given test location.

A "Graph" button 148 can be pressed to graph test results. FIG. 13 is an exemplary screen shot of a graph generated from test readings at a given test location.

Figure 14:
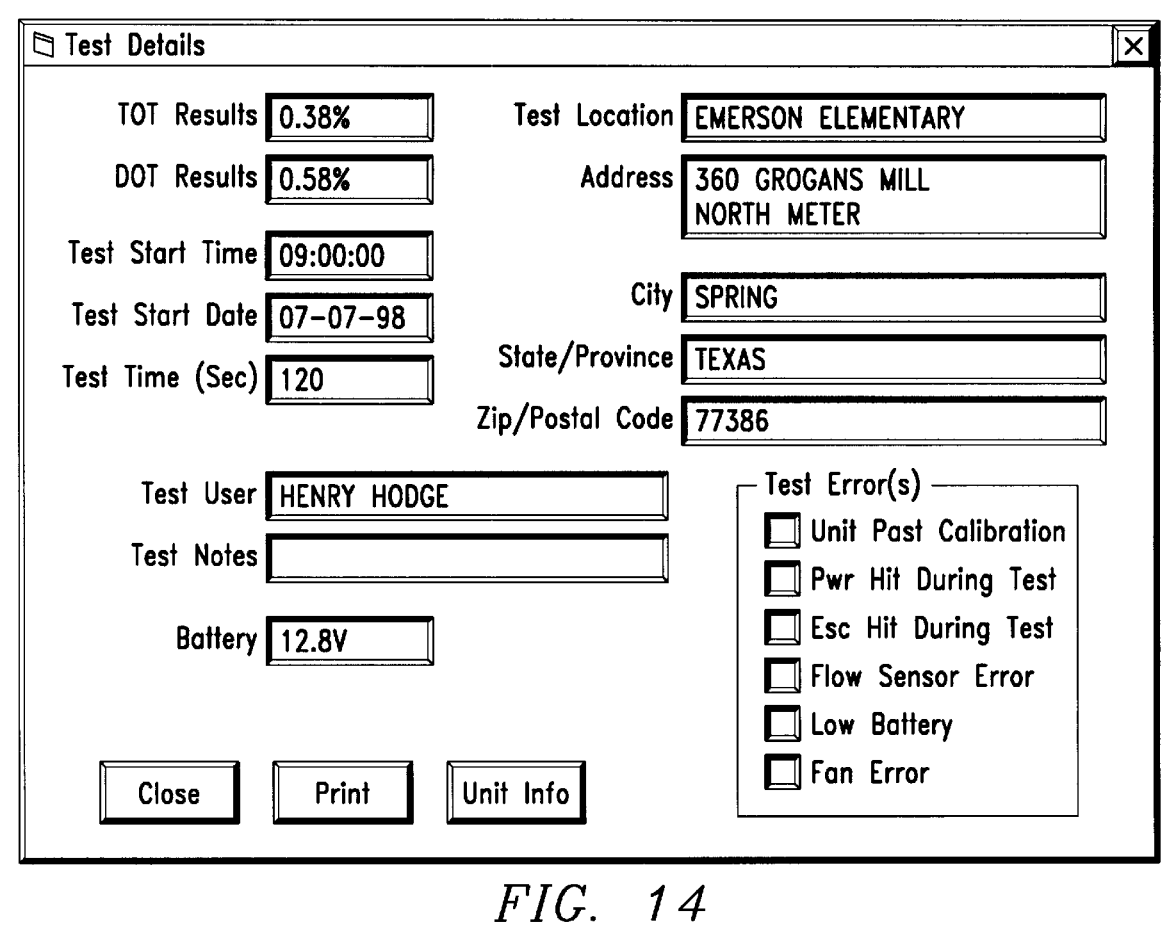

A "View Details" button 150 can be pressed if the user wishes to see complete data of a given test. FIG. 14 is an exemplary screen shot showing details of a given test conducted using the device.

A "Unit Information" button 152 can be pressed to view critical parameters of the device, e.g., calibration and error log data.

Figure 15:
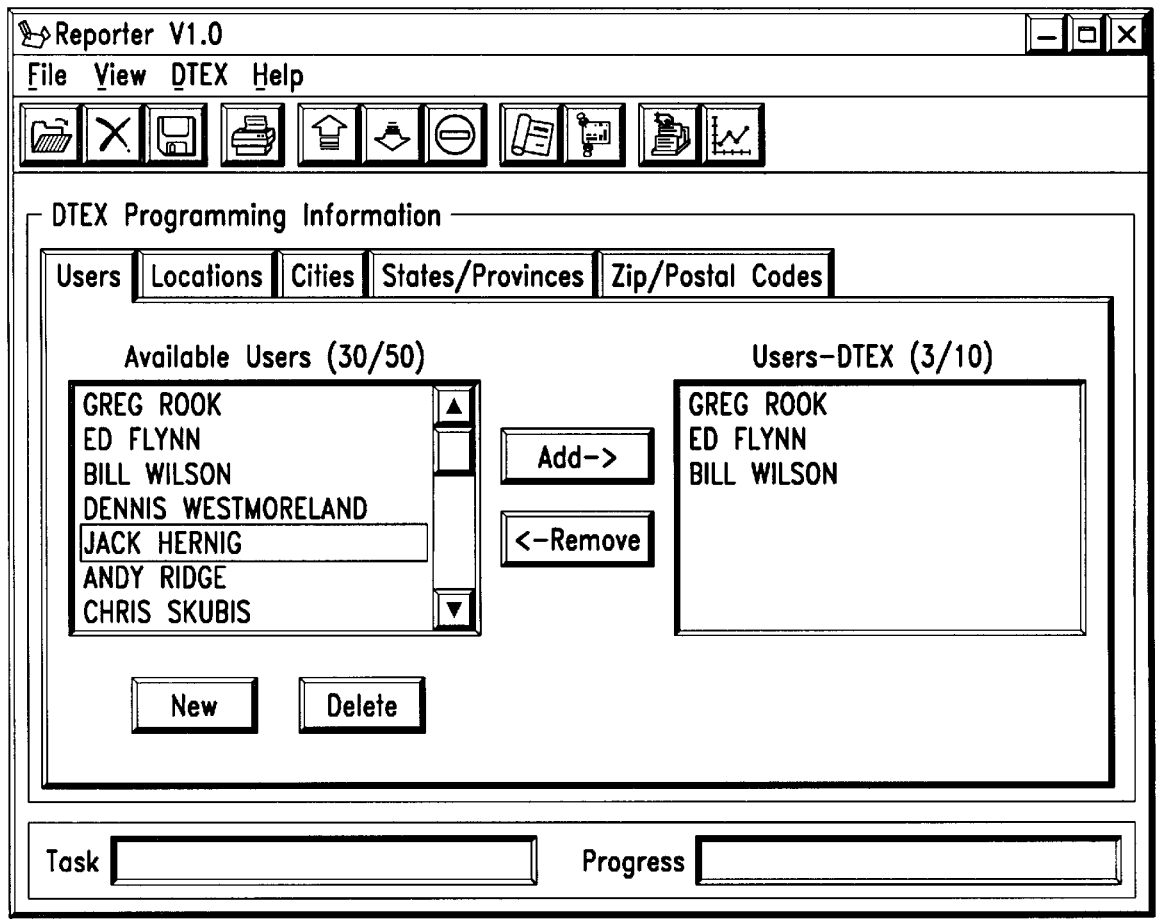
FIG. 15 is an exemplary screen shot generated by the PC software illustrating pre-loading of user and test location data on the device.

In the "View Programming Information" mode, the user can press an "Open File" button 154 to view a list of all files that have been uploaded to or downloaded from the device. FIG. 15 is an exemplary screen shot illustrating pre-loading of user and test location data on the device.

By pressing a "Save File" button 156, a user can save programming information including, e.g., configuration information. This information can be used to program another device in the same way as the subject device, which may, e.g., be in need of service.

The user can press an "Add Item" button 158 to add a programmable item to the master list such as, e.g., a new user and/or location. The user can also press an "Upload" button 160, which allows data to be uploaded to the device.

Figure 16:
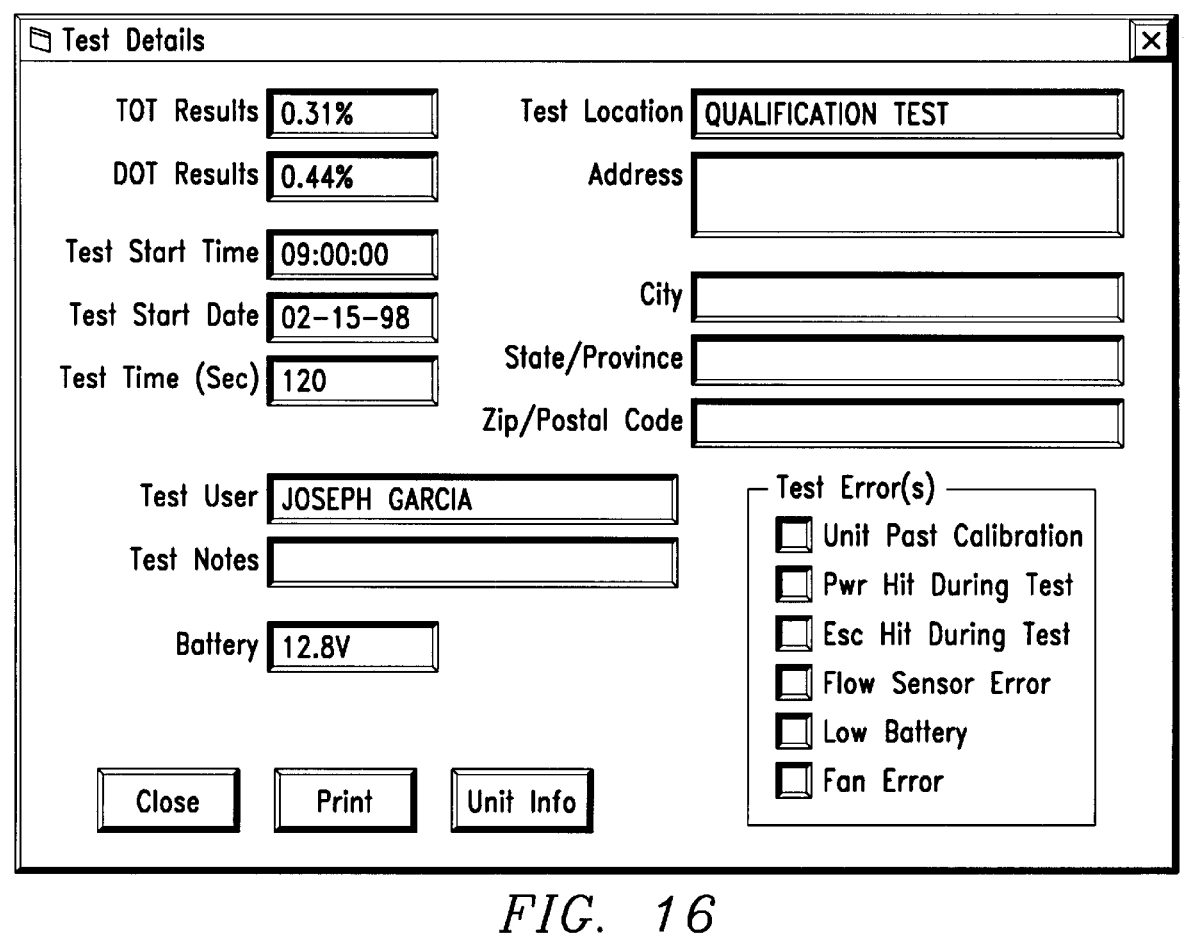
Figure 17:
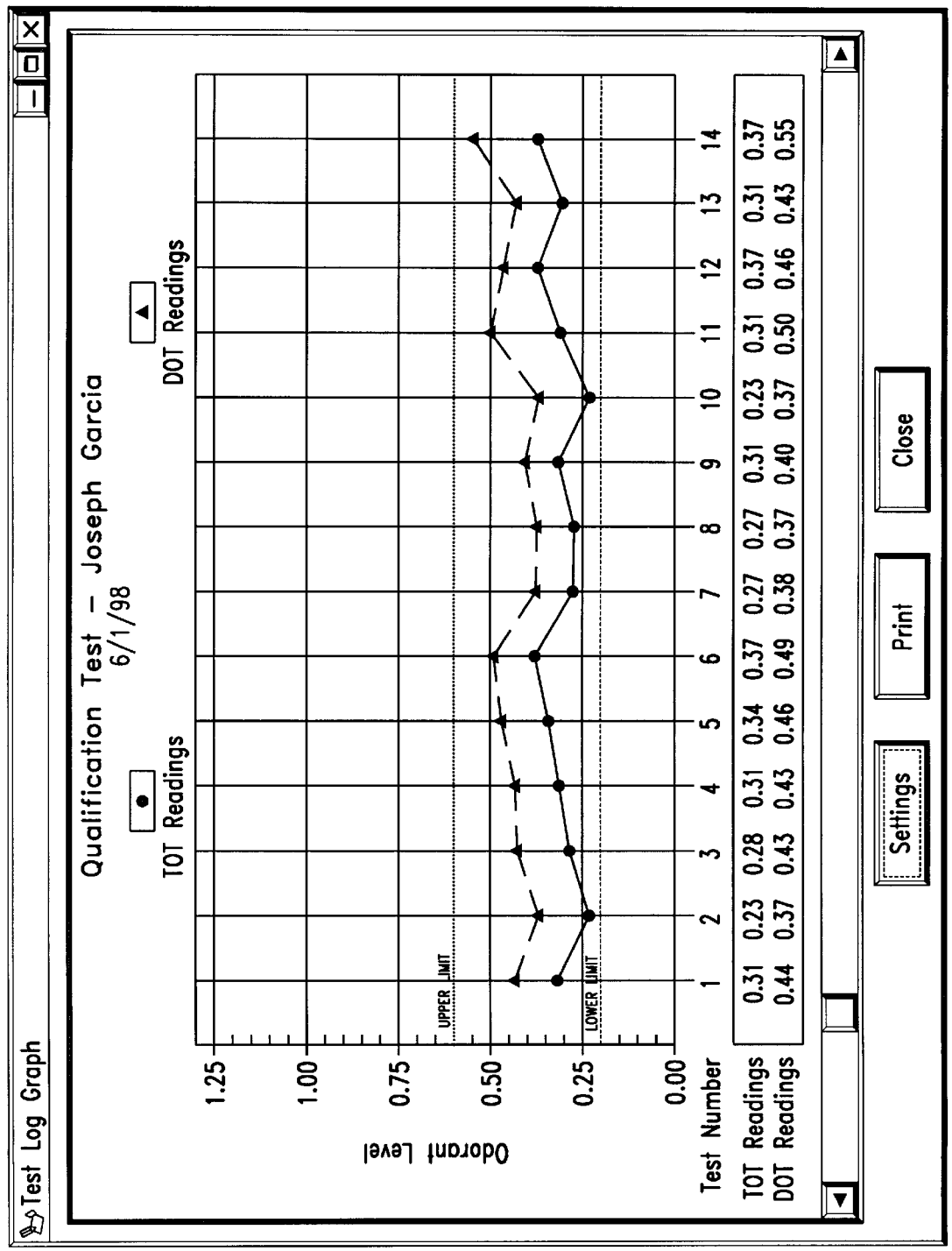
FIG. 17 is an exemplary screen shot generated by the PC software of a graph of the results of multiple qualification tests taken by a given user.

The device 10 can be used to test the smell sensitivity of technicians working in the industry since individuals will have varying sensitivity to odor. The automatic data recording feature helps prevent any test cheating by users. FIG. 16 is an exemplary screen shot showing details of a qualification test taken by a given user. FIG. 17 is an exemplary screen shot of a graph of the results of multiple qualification tests taken by a given user.

The software preferably comprises a set of instructions in a code module resident in a random access memory of the PC 108. Until required by the computer, the set of instructions may be stored in another computer memory such as a hard disk drive or in a removable memory such as an optical disk for eventual use in a CD ROM or a floppy disk for eventual use in a floppy disk drive, or even downloaded via the Internet.

In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the method steps.

Having thus described my invention, what I claim as new and desire to secure by Letters Patent is set forth in the following claims.

We claim:

1. A portable apparatus for determining odor levels in gas streams, comprising:
   a mixing chamber for mixing gas from a gas supply with ambient air to form a gas-air mixture, said mixing chamber including a gas inlet port through which the gas is received, an air intake port through which the air is received, and an outlet port through which the gas-air mixture exits said mixing chamber;
   a valve connectable to the gas supply enabling a user to selectively adjust flow of the gas from the gas supply to the apparatus;
   a mass flow sensor positioned between the flow control valve and the gas inlet port of said mixing chamber for measuring the mass flow rate of the gas flowing into the mixing chamber;
   a motorized fan for moving the gas-air mixture out of the mixing chamber to a location where said gas-air mixture can be sniffed by the user to detect odor;
   a controller for maintaining said motorized fan at a substantially constant given speed;
   a processor;
   a keypad for entry of data related to a given test;
   a display for displaying data related to a given test;
   a non-volatile memory operably coupled to the processor for storing the data related to the given test, the data including one or more of the following: an odor detection level, an operator identifier, a date and a timestamp of the test, a test location, a test time, operator-entered notes, and an indication of any test errors; and
   program means executable by the processor for restricting access by a user to the data stored in the non-volatile memory.

2. The portable apparatus of claim 1 wherein said controller includes a tachometer for determining rotational speed of the motorized fan.

3. The portable apparatus of claim 1 further comprising an infrared emitter and receiver pair positioned on opposite sides of said motorized fan for generating an infrared beam that is interruptable by movement of blades of said motorized fan.

4. The portable apparatus of claim 1 further comprising a mixing element at said air intake port of said mixing chamber for causing air flow turbulence to promote mixing of said air and gas.

5. The portable apparatus of claim 4 wherein said mixing element comprises a stationary fan.

6. The portable apparatus of claim 1 wherein said motorized fan is located in a conduit connected to the outlet port of the mixing chamber for drawing the gas-air mixture out of said mixing chamber.

7. The portable apparatus of claim 1 further comprising means for linearizing mass flow rate data generated by the mass flow sensor.

8. The portable apparatus of claim 1 further comprising a battery for powering the apparatus.

9. The portable apparatus of claim 8 wherein said battery is rechargeable.

10. The portable apparatus of claim 9 further comprising a charger port connected to said battery for enabling said battery to be recharged in situ.

11. The portable apparatus of claim 10 further comprising battery compensation circuitry for enabling said mass flow sensor to operate accurately within a given voltage range of said battery.

12. The portable apparatus of claim 1 further comprising means for linking said apparatus to a computer for transmitting data to and receiving data from said computer.

13. The portable apparatus of claim 1 further comprising means for linking said apparatus to a printer for printing data from said apparatus.

14. A system for performing odor testing, comprising:
   an odorometer comprising:
      a mixing chamber for mixing gas from a gas supply with air to form a gas-air mixture, the mixing chamber including a gas inlet port through which the gas is received, an air intake port through which the air is received, and an outlet port through which the gas-air mixture exits the mixing chamber;
      a motorized fan for moving the gas-air mixture out of the mixing chamber to a location where the gas-air mixture can be sniffed by the user to detect odor;
      a processor;
      a keypad for entry of data related to a given test;
      a display for displaying data related to a given test;
      a non-volatile memory operably coupled to the processor for storing the data related to the given test, the data including one or more of the following: an odor detection level, an operator identifier, a date and a timestamp of the test, a test location, a test time, operator-entered notes, and an indication of any test errors; and
      program means executable by the processor for restricting access by a user to the data stored in the non-volatile memory;
   a computer; and
   means for exchanging the data related to the given test between the odorometer and the computer.

15. The system of claim 14, wherein the computer includes means for processing and displaying the data related to the given test.

16. The system of claim 15, wherein said means for processing data include means for generating graphs from said data.

17. The system of claim 15, wherein said means for processing data include means for filtering said data.

18. The system of claim 14 wherein said computer includes means for archiving the data related to the given test.

* * * * *